United States Patent [19]

Hardman

[11] 4,131,631

[45] Dec. 26, 1978

[54] DEHYDROGENATION OF PARAFFINS

[75] Inventor: Harley F. Hardman, Lyndhurst, Ohio

[73] Assignee: Standard Oil Company, Cleveland, Ohio

[21] Appl. No.: 643,464

[22] Filed: Dec. 22, 1975

[51] Int. Cl.$^2$ .............................................. C07C 3/28
[52] U.S. Cl. ................................. 260/683.3; 252/470
[58] Field of Search ...................... 260/683.3, 680 E; 252/470

[56] References Cited

U.S. PATENT DOCUMENTS

| 3,159,688 | 12/1964 | Jennings et al. | 260/680 E |
|---|---|---|---|
| 3,248,451 | 4/1966 | Hughes | 260/683.3 |
| 3,692,860 | 9/1972 | Boutry et al. | 260/680 R |
| 3,806,446 | 4/1974 | Hayes | 208/138 |
| 3,900,430 | 8/1975 | Beaty, Jr. | 260/683.3 |
| 3,917,736 | 11/1975 | Frech et al. | 260/680 E |
| 3,972,954 | 8/1976 | Bertus | 260/683.3 |
| 3,980,721 | 9/1976 | Juguin et al. | 260/683.3 |
| 4,002,696 | 1/1977 | Hoppstock | 260/680 E |

*Primary Examiner*—O. R. Vertiz
*Assistant Examiner*—Wayne A. Langel
*Attorney, Agent, or Firm*—Herbert D. Knudsen; Evelyn R. Kosman

[57] ABSTRACT

A process for the dehydrogenation of paraffinic hydrocarbons containing from 3 to 6 carbon atoms to the corresponding monoolefin, wherein the process is carried out in the vapor phase, in the presence of oxygen and in the presence of an improved oxidative dehydrogenation catalyst containing cobalt and molybdenum.

15 Claims, No Drawings

DEHYDROGENATION OF PARAFFINS

This invention relates to a process for the dehydrogenation of paraffinic hydrocarbons to the corresponding monoolefins. More particularly, this invention relates to the dehydrogenation of paraffins containing 3 to 6 carbon atoms to the corresponding monoolefins, in the vapor phase, in the presence of oxygen and an improved oxidative dehydrogenation catalyst.

PRIOR ART

Oxidative dehydrogenation of paraffinic hydrocarbons has been previously described in U.S. Pat. No. 3,119,111 wherein alkanes containing 4 to 6 carbon atoms and having a 4-carbon chain are dehydrogenated to the 1,3-alkadienes in the presence of an oxygen-containing gas and an oxidative dehydrogenation catalyst comprising an alkali metal molybdate. British Patent No. 1,197,537 describes the oxidative dehydrogenation of paraffins to mono- and diolefins in the presence of oxygen and a catalyst containing the oxides of (a) molybdenum and/or tungsten and (b) chromium, manganese, iron, nickel or cadmium. U.S. Pat. No. 3,745,194 discloses the oxydehydrogenation of organic compounds utilizing catalysts containing tin in an oxidized state in combination with at least one of the metals, bismuth, cobalt or nickel in an oxidized state. U.S. Pat. No. 3,758,609 describes an oxydehydrogenation reaction with alkanes utilizing a catalyst containing cobalt-iron-antimony or nickel-iron-antimony in an oxidized state.

In the production of olefins by the catalytic dehydrogenation of paraffins, it is of course desirable to obtain as high a yield of olefin as possible in a single passage of the paraffin through the dehydrogenation zone. It is also desirable to conduct the reaction under such conditions and in the presence of such catalysts wherein a minimum amount of coke is formed on the catalyst. The advantage of the present process resides in the use of certain catalysts which maintain a high olefin selectivity in the presence of oxygen and wherein the oxygen is used to consume the coke. The required frequency of catalyst regeneration with the catalysts of this process is thereby greatly reduced or virtually eliminated.

THE INVENTION

The process of the present invention comprises the dehydrogenation of paraffins containing from three to six carbon atoms to the corresponding monoolefins, said dehydrogenation reaction being conducted in the vapor phase, in the presence of molecular oxygen or a molecular oxygen-containing gas and in the presence of a catalyst containing the oxides of cobalt and molybdenum and optionally an oxide or oxides of one or more of the elements selected from the group consisting of phosphorus and the metals of Groups IA, IIA, VIB, and VIII of the Periodic Classification. The process involves passing the paraffin and oxygen at a moderate temperature over a catalyst having the following composition:

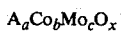

$A_a Co_b Mo_c O_x$ wherein A can be one or more elements selected from the group consisting of phosphorus and the metals of Groups IA, IIA, VIB and VIII of the Periodic Table, and wherein a is a number from 0 to 3, b is a number from 0.1 to 2, c is a number from 0.1 to 6, and x is a number determined by the valence requirements of the elements of A, Co and Mo.

Preferred are those catalysts wherein a is a number from 0.1 to 1.0, b is a number from 0.25 to 1.25, c is a number from 0.5 to 3; and x is a number determined by the valence requirements of the elements of A, Co and Mo. Especially preferred are those catalysts wherein A in the formula may be at least one element selected from the group consisting of potassium, magnesium, calcium, chromium, iron, nickel and phosphorus.

The catalyst useful in the instant process may be used alone or supported on or impregnated in a carrier material. Suitable carrier materials include alumina, silica, thoria, zirconia, titania, boron phosphate, silicon carbide, pumice, diatomaceous earth, clay, and the like. In general this support may be employed in amounts less than 95% by weight of the final catalyst composition.

The catalysts embodied herein may be calcined to produce desirable physical properties such as attrition resistance, optimum surface area and particle size. It is generally preferred that the calcined catalyst be further heat-treated in presence of oxygen and at a temperature above about 250° C., but below a temperature deleterious to the catalyst. The process of this invention is particularly applicable to the dehydrogenation of propane to propylene; n-butane to butene-1 and cis and trans-butene-2; isobutane to isobutylene; and isopentane to 2-methyl-2-butene, 2-methyl-1-butene and 3-methyl-1-butene. This process is also suitable for the dehydrogenation of ethylbenzene to styrene.

The reaction is carried out at elevated temperatures of from about 400° to 700° C. and more preferably in the range of from 500° to 650° C.

The pressure at which the instant process is usually conducted is about one atmosphere, although pressures of from slightly below atmospheric up to about 3 atmospheres are operable.

The apparent contact time employed in the instant process may be within the range of 0.1 to 25 seconds, and for good selectivity and yields a contact time of from 1 to 15 seconds is preferred.

An essential requirement in the present process is the presence of molecular oxygen or a molecular oxygen-containing gas such as air. Suitable molar ratios of the paraffin feed: oxygen may be in the range of from about 1:0.04 to 1:10 while the preferred molar ratios of paraffin: oxygen are in the range of about 1:0.1 and 1:1. Diluent gases such as nitrogen, steam, carbon dioxide or other inert gases may be present in minor amounts in the reaction mixture, and concentrations of up to 25 moles per mole of hydrocarbon fed may be present without having any deleterious effects on the reaction.

The reactor employed in this process may be either a fixed bed or a fluidized bed reactor.

A better understanding of the invention may be derived from the following specific examples. However, it is not to be construed that the instant invention is to be limited to these examples.

SPECIFIC EXAMPLES

Examples 1 to 5

Preparation of Catalyst (A) - 80% $CoMoO_4$ - 20% $SiO_2$ 97.5 g. of cobalt nitrate [$Co(NO_3)_2.6H_2O$] in 100 mls. of distilled water were added to a hot solution of 88.6 g. of $(NH_4)_6 Mo_7O_{24}.4H_2O$ in 100 mls. of water. 83.2

Grams of H. S. Ludox (silica sol) were then added and the slurry was evaporated to a consistency of thick paste. The mixture was dried at 120° C. for 16 hours, calcined at 427° C. for 6 hours, and then at 538° C. for 4 hours.

The catalyst was placed in a standard 20 cc. fixed bed reactor constructed of ⅜" O.D. stainless steel tubing. A ⅛" O.D. thermocouple well, located axially, allowed for temperature profile measurements. The reactor and a preheat loop were immersed in a controlled temperature salt bath, and temperatures recorded were the maximum temperatures reached in the catalyst bed. The catalyst volume was 20 cc. and the catalyst mesh size was 10 to 30 mesh per linear inch (U.S.A. Standard Sieve Series). The hydrocarbon feed employed in the examples was propane. A mixture of propane and air (with the exception of Example 1) in various molar ratios was passed over the catalyst at a temperature of 538° C. and at a rate so that the contact time was equivalent to 3 seconds. In Example 1, only propane was contacted with the catalyst. The reactor effluent passed through an air-cooled condensation pot and a "Drierite" tube before sampling and metering. Hydrogen in the effluent stream was determined by gas chromatography, using a 3-foot molecular sieve column at ambient temperature with an argon carrier gas. Other components of the effluent were analyzed by the Fisher Gas Partitioner, using the standard HMPA-molecular sieve column combination.

The conversions obtained in these examples are shown in Table 1. The percent conversion in the table represents the total propane converted to propylene and to other products (total propane converted per pass); per pass conversion to propylene represents the percent propane converted to propylene in a single pass; and selectivity to propylene is the percent of propylene obtained based on propane converted, all percents being calculated on molar basis.

The data in Table 1 unexpectedly show that percent conversion of propane and selectivity to propylene are not adversely affected by the presence of oxygen in the reaction.

Example 6

The oxydehydrogenation procedure in Examples 2 to 5 was repeated using catalyst (B), with the exception that the air/propane ratio on a molar basis was 2.5.

Preparation of Catalyst (B) - 60% $CoMoO_4$ - 40% $SiO_2$ 79.7 g. cobalt nitrate $[Co(NO_3)_2.6H_2O]$ in water solution was added to a hot aqueous solution of 48.3 g. of $(NH_4)_6Mo_7O_{24}.4H_2O$ in 200 mls. of water. 100 g. of Nalco 40% silica sol were added and the entire mixture with stirring was evaporated to a thick paste and dried at 110° C. The dried catalyst was calcined at 427° C. for 5 hours and then at 649° C. for 4 hours.

Example 7

The oxydehydrogenation procedure in Example 6 was repeated using catalyst (C).

Preparation of Catalyst (C) - 60% $CoP_{0.2}MoO_x$ - 40% $SiO_2$ 5.92 g. of 85 phosphoric acid were dissolved in 200 cc. of boiling water. To this were added with stirring 45.4 g. of $(NH_4)_6P_6Mo_7O_{24}.H_2O$, 74.8 g. of $Co(NO_3)_2.6H_2O$ dissolved in 250 cc. of water, and 100 g. of 40% silica. The mixture was evaporated to a thick paste and dried at 110° C., then calcined at 593° C. for 24 hours.

Example 8

The oxydehydrogenation procedure in Example 6 was repeated utilizing catalyst (D).

Preparation of Catalyst (D) - 60% $Co_{0.5}Ni_{0.5}MoO_x$ - 40% $SiO_2$ 39.9 g. of $Co(NO_3)_2.6H_2O$, 39.8 g. $Ni(NO_3)_2.6H_2O$, 48.4 g. of $(NH_4)_6Mo_7O_{24}.4H_2O$, and 100 g. 40% $SiO_2$ were combined as in Catalyst (C) and the mixture was dried and calcined in the same manner.

Example 9

The oxydehydrogenation procedure in Example 6 was repeated using catalyst (E).

Preparation of Catalyst (E) - 60% $Co_{0.5}Fe_{0.5}MoO_x$ - 40% $SiO_2$ 48.7 g. of $(NH_4)_6Mo_7O_{24}.4H_2O$ were dissolved in 200 cc. of boiling water, and to this were added with stirring 40.2 g. $Co(NO_3).6H_2O$, 55.75 g. $Fe(NO_3)_3.9H_2O$ in 250 cc. of water, and 100 g. of 40% $SiO_2$ (Nalco). The mixture was evaporated to a thick paste and then dried overnight in an oven at 110° C. The dried catalyst was then calcined at 427° C. for 4 hours and subsequently at 593° C. for 24 hours.

Example 10

The oxydehydrogenation procedure in Example 6 was repeated utilizing catalyst (F).

Preparation of Catalyst (F) - 60% $Co_{0.5}Mg_{0.5}MoO_x$ - 40% $SiO_2$ 43.4 g. $Co(NO_3)_2.6H_2O$, 38.2 g. $Mg(NO_3)_2.6H_2O$, 52.6 g. $(NH_4)_6Mo_7O_{24}.4H_2O$, and 100 g. 40% $SiO_2$ (Nalco) were combined as in catalyst (E) and the catalyst was calcined at 593° C. for 4 hours.

Example 11

The oxydehydrogenation procedure of Example 6 was repeated using catalyst (G).

Preparation of Catalyst (G) - 60% $Co_{0.75}Mg_{0.25}P_{0.2}MoO_x$ - 40% $SiO_2$ 58.4 g. $Co(NO_3)_2.6H_2O$, 17.1 g. $Mg(NO_3)_2.6H_2O$, 47.2 g. $(NH_4)_6Mo_7O_{24}.4H_2O$, 6.165 g. 85% $H_3PO_4$ and 100.0 g. 40% $SiO_2$ were combined, dried and calcined as in catalyst (C) with the exception that the dried catalyst was calcined for 4 hours at 427° C. and 4 hours at 593° C.

Example 12

The oxydehydrogenation procedure of Example 6 was repeated using catalyst (H).

Preparation of Catalyst (H) - 60% $K_{0.16}CoP_{0.2}MoO_x$ - 40% $SiO_2$ 0.432 g. $KNO_3$, 74.67 g. $Co(NO_3)_2.6H_2O$, 45.3 g. $(NH_4)_6Mo_7O_{24}.4H_2O$, 5.92 g. 85% $H_3PO_4$ and 100 g. 40% $SiO_2$ were combined, dried and calcined as in catalyst G.

Example 13

The oxydehydrogenation procedure of Example 6 was repeated using catalyst (I).

Preparation of Catalyst (I) - 60% $Co_{0.5}Ni_{0.25}Mg_{0.25}P_{0.2}MoO_x$ - 40% $SiO_2$ 38.9 g. $Co(NO_3)_2.6H_2O$, 19.4 g. $Ni(NO_3)_2.6H_2O$, 17.1 g. $Mg(NO_3)_2.6H_2O$, 6.16 g. 85% $H_3PO_4$, 47.2 g. $(NH_4)_6Mo_7O_{24}.4H_2O$ and 100 g. 40% $SiO_2$ were combined, dried and calcined in the same manner as in catalyst (G).

The percent conversions of propane to propylene and the percent selectivities to propylene obtained in Examples 6 to 13 are summarized in Table II.

Table I

Effect of Air/Hydrocarbon Ratio on Conversion of Propane to Propylene

| Example No. | Mole Ratio Air/$C_3$ | % Per Pass Conversion (Total) | % Per Pass Conver. to $C_3^=$ | % Selectivity to $C_3^=$ |
|---|---|---|---|---|
| 1 | 0 | 1.1 | 0.7 | 63.6 |
| 2 | 0.2 | 4.1 | 3.2 | 77.9 |
| 3 | 1 | 9.4 | 6.2 | 65.9 |
| 4 | 1.8 | 9.8 | 6.4 | 65.3 |
| 5 | 2.5 | 20.7 | 11.3 | 54.7 |

Table II

Effect of Catalyst Composition on the Conversion of Propane to Propylene

| Example No. | % Per Pass Conversion (Total) | % Per Pass Conversion to $C_3^=$ | % Selectivity to $C_3^=$ |
|---|---|---|---|
| 6 | 8.4 | 5.2 | 61.9 |
| 7 | 25.0 | 14.0 | 58.0 |
| 8 | 13.3 | 8.5 | 63.9 |
| 9 | 15.4 | 6.2 | 40.2 |
| 10 | 12.9 | 8.5 | 65.9 |
| 11 | 24.3 | 11.7 | 48.2 |
| 12 | 18.2 | 8.9 | 49.4 |
| 13 | 23.5 | 11.4 | 48.5 |

I claim:

1. The process for the dehydrogenation of paraffinic hydrocarbons containing from 3 to 6 carbon atoms to the corresponding monoolefins comprising contacting said paraffinic hydrocarbon with molecular oxygen, at a temperature of from about 400° to 700° C and a pressure of from about 1 up to about 3 atmospheres, over a catalyst having the composition:

$$A_a Co_b Mo_c O_x$$

wherein A is one or more of the elements selected from the group consisting of phosphorus and the metals of Groups IA, IIA, VIB and VIII of the Periodic Table, and wherein said catalyst contains at least one element of Group IA or Group IIA;

and wherein a = a number from greater than 0 to 3;

b = a number from 0.1 to 2, c = a number from 0.1 to 6, and x is the number of oxygens determined by the valence requirements of the other elements present.

2. The process in claim 1 wherein the catalyst is supported on a carrier material.

3. The process in claim 1 wherein the molar ratio of paraffin to oxygen is in the range of from about 1:0.04 to 1:10.

4. The process in claim 3 wherein the contact time is in the range of from about 0.1 to 25 seconds.

5. The process in claim 4 wherein the paraffinic hydrocarbon is propane.

6. The process in claim 4 wherein the paraffinic hydrocarbon is isobutane.

7. The process in claim 4 wherein the paraffinic hydrocarbon is n-butane.

8. The process in claim 4 wherein the dehydrogenation reaction is carried out in the vapor phase.

9. The process in claim 4 wherein a in the formula is a number from 0.1 to 1.0, b is a number from 0.25 to 1.25, and c is a number from 0.5 to 3.

10. The process in claim 9 wherein A in the formula is at least one element selected from the group consisting of phosphorus, potassium, chromium, magnesium, calcium, iron and nickel.

11. The process in claim 1 wherein A in the catalyst formula is a Group IA metal.

12. The process in claim 11 wherein the catalyst composition also contains phosphorus.

13. The process in claim 1 wherein A in the catalyst formula is a Group IIA metal.

14. The process in claim 11 wherein the catalyst composition also contains phosphorus.

15. The process in claim 14 wherein the catalyst composition also contains iron or nickel or both.

* * * * *